US011439579B2

(12) United States Patent
Bonnet et al.

(10) Patent No.: US 11,439,579 B2
(45) Date of Patent: Sep. 13, 2022

(54) POLYMER OF HYALURONATE AND OF GLUCOMANNAN

(71) Applicant: BASF Beauty Care Solutions France SAS, Lyons (FR)

(72) Inventors: Isabelle Bonnet, Lyons (FR); Florent Durieux, Cremieu (FR); Eric Nappi, Lyons (FR)

(73) Assignee: BASF Beauty Care Solutions France SAS, Lyons (FR)

( * ) Notice: Subject to any disclaimer, the term of this patent is extended or adjusted under 35 U.S.C. 154(b) by 0 days.

(21) Appl. No.: 14/438,251

(22) PCT Filed: Oct. 24, 2013

(86) PCT No.: PCT/FR2013/052546
§ 371 (c)(1),
(2) Date: Apr. 24, 2015

(87) PCT Pub. No.: WO2014/064391
PCT Pub. Date: May 1, 2014

(65) Prior Publication Data
US 2015/0283055 A1 Oct. 8, 2015

Related U.S. Application Data

(60) Provisional application No. 61/718,765, filed on Oct. 26, 2012.

(30) Foreign Application Priority Data

Oct. 25, 2012 (FR) ...................................... 1260164

(51) Int. Cl.
*A61K 8/73* (2006.01)
*A61Q 19/08* (2006.01)
(Continued)

(52) U.S. Cl.
CPC .............. *A61K 8/735* (2013.01); *A61K 8/025* (2013.01); *A61K 9/0014* (2013.01); *A61K 9/107* (2013.01);
(Continued)

(58) Field of Classification Search
CPC ...... A61K 47/36; A61K 8/025; A61K 31/736; A61K 31/728; A61K 31/738; A61K 8/735;
(Continued)

(56) References Cited

U.S. PATENT DOCUMENTS 5,562,924 A 10/1996 Perrier et al.
5,672,301 A * 9/1997 Orly .................. B01J 13/08
264/4.1
(Continued)

FOREIGN PATENT DOCUMENTS

CN 102380129 A 3/2012
FR 2688422 A1 9/1993
(Continued)

OTHER PUBLICATIONS

"Each other", Garner's Modern English Usage, Garner, ed., Oxford University Press, 2016.*
(Continued)

*Primary Examiner* — Timothy P Thomas
(74) *Attorney, Agent, or Firm* — Faegre Drinker Biddle & Reath LLP

(57) ABSTRACT

The present invention concerns a sphere, characterized in that it comprises at least one polymer of hyaluronate and glucomannan. It also concerns a polymer of hyaluronate and glucomannan characterized in that each bond between a hyaluronate group and a glucomannan group is an ester bond. In addition, it concerns their production process and their use, in particular as a filling or hydration agent.

21 Claims, 4 Drawing Sheets

(51) Int. Cl.

| | |
|---|---|
| A61K 31/728 | (2006.01) |
| A61K 31/736 | (2006.01) |
| A61K 31/738 | (2006.01) |
| A61Q 19/00 | (2006.01) |
| C08B 37/08 | (2006.01) |
| C08L 5/08 | (2006.01) |
| C08L 5/00 | (2006.01) |
| C08B 37/00 | (2006.01) |
| C08J 3/24 | (2006.01) |
| A61K 9/107 | (2006.01) |
| A61K 9/00 | (2006.01) |
| A61K 47/32 | (2006.01) |
| A61K 9/50 | (2006.01) |
| A61K 47/36 | (2006.01) |
| A61K 8/02 | (2006.01) |

(52) U.S. Cl.
CPC .......... *A61K 9/5036* (2013.01); *A61K 31/728* (2013.01); *A61K 31/736* (2013.01); *A61K 31/738* (2013.01); *A61K 47/32* (2013.01); *A61K 47/36* (2013.01); *A61Q 19/00* (2013.01); *A61Q 19/007* (2013.01); *A61Q 19/08* (2013.01); *C08B 37/009* (2013.01); *C08B 37/0072* (2013.01); *C08B 37/0087* (2013.01); *C08J 3/246* (2013.01); *C08L 5/00* (2013.01); *C08L 5/08* (2013.01); *A61K 2800/412* (2013.01); *A61K 2800/546* (2013.01); *C08J 2305/00* (2013.01); *C08J 2305/08* (2013.01); *Y10T 428/2982* (2015.01)

(58) Field of Classification Search
CPC .......... A61K 2800/412; C08B 37/0087; C08B 37/009; C08B 37/0072; C08J 3/246
See application file for complete search history.

(56) References Cited

U.S. PATENT DOCUMENTS

| | | | |
|---|---|---|---|
| 6,132,750 A * | 10/2000 | Perrier | A61K 47/6927 424/418 |
| 8,906,425 B2 | 12/2014 | Perrier et al. | |
| 2004/0096925 A1 | 5/2004 | Perrier et al. | |
| 2006/0069032 A1 | 3/2006 | Catroux et al. | |
| 2006/0188465 A1 | 8/2006 | Perrier et al. | |
| 2007/0184012 A1 | 8/2007 | Perrier et al. | |
| 2008/0038780 A1 * | 2/2008 | Stocks | C12P 19/26 435/84 |
| 2010/0255076 A1 * | 10/2010 | Heber | A61K 8/73 424/450 |
| 2013/0078202 A1 | 3/2013 | Abdul-Malak et al. | |

FOREIGN PATENT DOCUMENTS

| | | | |
|---|---|---|---|
| FR | 2847267 A1 | 5/2004 | |
| FR | 2855968 A1 | 12/2004 | |
| FR | 2882366 A1 | 8/2006 | |
| FR | 2893252 A1 | 5/2007 | |
| GB | 244036 A | 4/1926 | |
| WO | WO-0241877 A1 * | 5/2002 | .......... A61K 9/5036 |
| WO | WO-2009007411 A2 | 1/2009 | |
| WO | WO-2009043111 A1 | 4/2009 | |
| WO | WO-2009121422 A1 | 10/2009 | |

OTHER PUBLICATIONS

CA International Search Report for PCT/FR2013/052546 dated Dec. 5, 2013.
Chen, J., et al., "Investigation of Sodium hyaluronate / Konjac glucomannan blend films", Advanced Materials Research, 2012, vol. 510, pp. 673-678.
Japanese Office Action with English Translation for Japanese Application No. 2015-538535, dated Aug. 23, 2017.
Partial English translation of Wang, J. X. et al., Natural Functional Ingredients in Cosmetics, pp. 100-103, 2006.

* cited by examiner

POLYMER OF HYALURONATE AND OF GLUCOMANNAN

CROSS-REFERENCE TO RELATED APPLICATIONS

This application is a national stage application (under 35 U.S.C. § 371) of PCT/FR2013/052546, filed Oct. 24, 2013, which claims benefit of French Application No. 1260164, filed Oct. 25, 2012, and U.S. Application No. 61/718,765, filed Oct. 26, 2012, all of which are incorporated herein by reference in their entirety.

BACKGROUND OF THE INVENTION

(1) Field of Invention

The present invention relates to the cosmetics and dermatological field, and more particularly relates to novel spheres comprising at least one polymer of hyaluronate and glucomannan, as well as to their uses in topical application, in particular cosmetic or dermatological uses.

(2) Description of Related Art

Aging is a natural phenomenon which is inevitably accompanied by a reduction in cellular activity in the human body. The most visible signs of aging appear in the face: the skin slackens and the first wrinkles are formed and become visible.

Many solutions have been developed in order to attempt to fill wrinkles and mask them.

In its patent FR2688422, the Applicant describes a process for the production of microspheres by interfacial cross-linking of polysaccharide compounds.

The Applicant has also developed microspheres formed by a high molecular weight sodium hyaluronate mixture that is currently marketed and sold under the name FILLING SPHERES™ hyaluronic is from BASF. These microspheres, used in the dehydrated form, penetrate into the skin where they are rehydrated, thereby regaining their initial volume. Once filled out, they have multiplied to ten times their size in one hour. By filling out at the contours of the skin, they firm it up and fill the furrows of the wrinkles, making them less visible. Thus, FILLING SPHERES™ hyaluronic reduce wrinkles in a mechanical manner.

The Applicant has now discovered novel filling spheres that are more effective than those of the prior art, in particular than FILLING SPHERES™ hyaluronic.

These novel spheres comprise a polymer of hyaluronate and glucomannan.

The Applicant has also developed microspheres formed by a high molecular weight sodium hyaluronate mixture that is currently marketed and sold under the name FILLING SPHERES™ hyaluronic. These microspheres, used in the dehydrated form, penetrate into the skin where they are rehydrated, thereby regaining their initial volume. Once filled out, they have multiplied to ten times their size in one hour. By filling out at the contours of the skin, they firm it up and fill the furrows of the wrinkles, making them less visible. Thus, FILLING SPHERES™ hyaluronic reduce wrinkles in a mechanical manner.

The Applicant has now discovered novel filling spheres that are more effective than those of the prior art, in particular than FILLING SPHERES™ hyaluronic.

These novel spheres comprise a polymer of hyaluronate and glucomannan.

Glucomannan has been described in application WO2009043111 as a compound that is capable of inducing the accumulation of fibroblasts, in particular for tissue regeneration and for cicatrisation. It can then be administered with another compound of the collagen or polysaccharide type, including hyaluronic acids cross-linked with themselves and of high molecular weight (RESTYLANE™ and PERLANE™). That document also indicates that glucomannan may be cross-linked with hyaluronic acid, but gives butanediol diglycidyl ether cross-linking agents as the only example, which means that the bond between the hyaluronic acid and glucomannan groups will be of the ether type. Further, only one example is given of this type of polymer (Example 3). In that example, the polymer cross-linked with butanediol diglycidyl ether is in the form of an intradermally injected gel. Indeed, it is impossible to obtain microspheres with the cross-linking agent used in this example. Therefore, the polymer is always in the form of a gel. The only reference to glucomannan nanospheres is given in that document in one example, (4). Those nanospheres are hydrated glucomannan, chitosan and hyaluronic acid nanospheres in the form of a polyelectrolytic complex, i.e. not cross-linked and thus not having any covalent bonds, in particular between the glucomannan and the hyaluronic acid, which pass through the epidermis. Moreover, these nanospheres are nanoparticles and not nanocapsules, even less microcapsules or microspheres. Moreover, glucomannan must be inside the spheres, thus not being constitutive of their wall as glucomannan is neutral, whereas the polyelectrolytic complex is being formed between chitosan, positively charged, and hyaluronic acid, negatively charged. Thus, that application does not describe any spheres containing a polymer of glucomannan and hyaluronate (particularly which of the wall contains such a polymer), particularly any microsphere or microcapsule. Further, that application does not describe any polymers of glucomannan and hyaluronate cross-linked by an ester bond.

Further, the swell properties of glucomannan, including in its cross-linked form with hyaluronic acid, were not studied in that document and could not be, since it is always administered in the hydrated form.

In order to be active, the glucomannan of that document must act at the dermis where the fibroblasts are located and is thus formulated in the hydrated form, such as in highly viscous gels used by intradermal injection and in cosmetic compositions that are capable of reaching the dermis, such as in nanospheres. The techniques for filling by intradermal injection described in that document are expensive, invasive, and may in some cases give rise to an irreversible result, or may generate other secondary effects of an infection or allergic type. In addition, the skilled person knows the disadvantages of using compounds that penetrate the dermis, in particular in terms of allergies and secondary effects. The skilled person is also aware of the disadvantages of using compounds that act on biological targets, as opposed to compounds that act mechanically.

The application FR2882366 discloses cross-linked polymers of carbohydrate, such as polysaccharides, polyols and oligosaccharides. Glucomannan and hyaluronic acid are described among a long list of polysaccharides and no specific example of a polymer made of glucomannan and hyaluronic acid is given. Moreover, no example is even given of a polymer made of two different polysaccharides or even made only of hyaluronic acid or glucomannan. On the other way, the process disclosed does not give rise to microcapsules or microspheres, as indicated page 5, lines 13-25. Said process therefore is not an interfacial cross-linking, but a process of cross-linking in an aqueous phase, thus not allowing to obtain spheres.

SUMMARY OF THE INVENTION

The invention relates to a sphere formed by at least one polymer of hyaluronate and glucomannan, said polymer comprising at least one hyaluronate group and at least one glucomannan group, said hyaluronate group and said glucomannan group being cross-linked to one another optionally via a group originating from a cross-linking agent.

Thus, the present invention resolves the technical problem consisting of providing a novel ingredient that can be applied topically and that is more effective than the mechanical filling out ingredients of the prior art, in particular FILLING SPHERES™ hyaluronic.

Further, this ingredient must act on mechanical filling out at the epidermis, and thus without going via the biological skin pathways, and in particular without penetrating the dermis.

Finally, this cosmetic or dermatological ingredient should be easy to manufacture and formulate, it must be stable when formulated and it must be tolerated well by the skin.

Particularly surprisingly and unexpectedly, the Applicant has discovered that spheres of a polymer of hyaluronate and glucomannan solve each of these technical problems.

A BRIEF DESCRIPTION OF THE FIGURES

Figure 1:
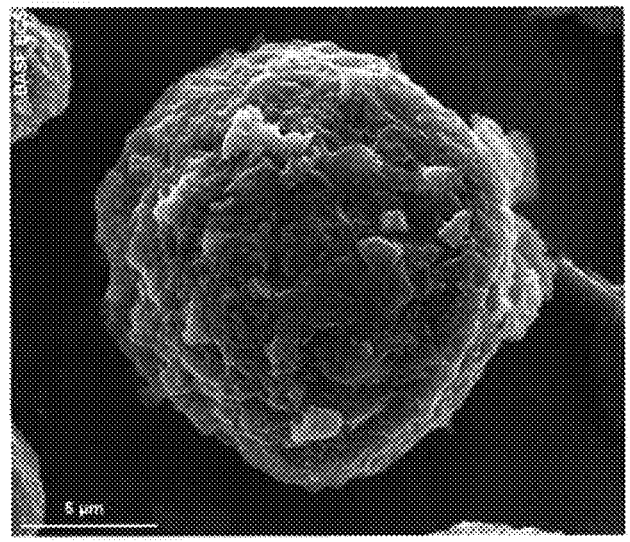
FIG. 1 represents a scanning electron microscope photograph of spheres in accordance with the invention in the dehydrated form obtained in Example 1.

In effect, the spheres and the polymer of the invention have exceptional filling out capacities. As will be demonstrated in Example 4, the spheres of the invention thus capture 41% more water and thus fill out 4 times more than FILLING SPHERES™ hyaluronic.

The spheres and the polymer of the invention have a higher water capture capacity, fill out better, more rapidly, and then retain the captured water better. When they penetrate the upper layers of the epidermis, the polymer and the spheres rehydrate in the presence of water and regain their initial volume. In addition, because of this capacity to attract and retain water at the epidermis, the polymer and the spheres of the invention are excellent agents for improving hydration of the skin and/or the mucous membranes, resulting in an improvement in the viscoelastic properties of the skin and/or the mucous membranes, in particular suppleness, firmness and elasticity. They are thus excellent cosmetic ingredients for preventing and/or treating the appearance of wrinkles in the epidermis.

Further, the spheres and the polymer of the invention are particularly resistant to washing and to dehydration. Comparative example 1 demonstrates that microspheres of glucomannan polymer do not have this property. The polymer of glucomannan and hyaluronate of the invention has a higher density and thus an increased resistance. This property of resistance to washing and to dehydration is further improved when the spheres are obtained by interfacial cross-linking polymerization.

The Applicant has thus demonstrated the importance of the choice of polymer groups, namely the hyaluronate and the glucomannan, so that it and the spheres that comprise it have an optimized density, are easy to synthesize and formulate, and are resistant as well as highly effective.

They are also entirely suited to topical use, and formulated in an appropriate cosmetic or dermatological composition of the invention, and they rehydrate in contact with the skin and/or the mucous membranes and/or in the epidermis, thereby providing maximum in situ efficacy. They are also particularly stable on the skin and/or the mucous membranes and thus can be long-lasting in their action.

The microspheres and the polymer of the invention are also eminently well tolerated by the skin and/or the mucous membranes because of the natural origins of the hyaluronate and the glucomannan, which makes them entirely biocompatible for topical application. In addition, their efficacy rests on their mechanical properties of superficial filling of the surface of the skin and/or the mucous membranes and of filling out in the upper layers of the epidermis.

The spheres of the invention, in particular the microspheres, in particular microcapsules, may also be very well suited to encapsulation and/or vectorization of active principles of cosmetic or dermatological interest.

The polymer and the spheres of the invention thus have the advantage of being effective on various levels: as a filling agent at the surface of the skin and/or mucous membranes on the one hand, as a filling out agent in the epidermis on the other hand, but also as a hydrating agent and/or as a means for delivering an active principle of cosmetic or dermatological interest, in particular by vectorization, in particular an active principle having complementary properties, such as anti-wrinkle properties and/or hydrating properties.

Thus, in a first embodiment, the present invention concerns a sphere, characterized in that it comprises at least one polymer of hyaluronate and glucomannan.

Advantageously, the sphere of the invention is characterized in that in the polymer, the hyaluronate group and the glucomannan group are bonded via at least one ester bond, and possibly a group deriving from the cross-linking agent, and are preferably bonded by two ester bonds and a group originating from the cross-linking agent.

Advantageously, the sphere of the invention is characterized in that the hyaluronate group has a low weight average molecular weight, advantageously in the range 5 kDa to 200 kDa, preferably in the range 10 kDa to 40 kDa. Indeed, for high molecular weight, it seems more difficult to obtain the spheres according to the invention because they tend to break (cf. example 3). Moreover, the yield of producing the spheres according to the invention is better with very low molecular weight hyaluronate (10-40 kDa) (cf. examples 1 and 2).

In particular, the sphere of the invention is characterized in that it is dehydrated; advantageously, its water content is 0.1% to 50%, preferably 1% to 20%, and more preferably 3% to 15% by weight. This water content may be measured using the Karl Fisher method.

In a second embodiment, the sphere of the invention is characterized in that it is obtainable, advantageously is obtained, by cross-linking, preferably interfacial, between a hyaluronate compound and a glucomannan compound, preferably in an emulsion. Advantageously, the cross-linking agent used for interfacial cross-linking is terephthalic acid dichloride.

In a third embodiment, the sphere of the invention is characterized in that the glucomannan group of the polymer is obtained from a konjac glucomannan, a salt or a derivative. Advantageously, the glucomannan group of the polymer has a molecular weight in the range 200 kDa to 2000 kDa.

In a fourth embodiment, the sphere of the invention is characterized in that the hyaluronate group of the polymer is obtained from a hyaluronate compound, preferably hyaluronic acid, a salt or a derivative of hyaluronic acid, preferably sodium hyaluronate.

In a fifth embodiment, the sphere of the invention is characterized in that it has a diameter of 1 µm to 1000 µm, preferably 1 µm to 300 µm, more preferably 3 µm to 80 µm. The term "diameter" preferably refers to the D50 diameter, more preferably the D90 diameter as conventionally measured in granulometry. Preferably, the granulometry is measured by laser diffraction, in particular using a Mastersizer 3000™ (Malvern) apparatus.

In a sixth embodiment, the present invention also concerns a polymer of hyaluronate and glucomannan, characterized in that each bond between a hyaluronate group and a glucomannan group is an ester bond.

Advantageously, the polymer of the invention is obtainable by cross-linking by means of an ester bond between a hyaluronate compound and a glucomannan compound, advantageously using a cross-linking agent that is preferably selected from acid dichlorides, in particular terephthalic, sebacic, succinic and fumaric acid dichloride or a mixture thereof, more preferably terephthalic acid dichloride.

In particular, the polymer of the invention is as defined above in the context of embodiments concerning spheres.

In a seventh embodiment, the present invention also concerns the use of a polymer of hyaluronate and glucomannan, preferably in accordance with the sixth embodiment of the present invention, and/or a sphere in accordance with the present invention, as an agent for filling out the epidermis and/or to fill the epidermis, and/or to plump the epidermis, and/or to improve hydration of the skin and/or the mucous membranes, and/or to encapsulate or vectorize another ingredient of cosmetic interest.

In an eighth embodiment, the present invention concerns the use of a polymer in accordance with the fifth embodiment, and/or of a sphere in accordance with the present invention, as an agent for filling out the epidermis and/or to fill the epidermis and/or to smooth the contours of the skin and/or to plump the epidermis and/or to improve the elasticity of the skin and/or the mucous membranes and/or to prevent and/or treat the appearance of wrinkles in the epidermis, in particular superficial wrinkles.

In addition, in an eighth embodiment, the present invention concerns a cosmetic or dermatological composition for topical administration, comprising at least one sphere in accordance with the present invention and/or a polymer in accordance with a sixth embodiment, and a cosmetically or dermatologically appropriate vehicle.

Advantageously, the polymer and/or the sphere is included in the composition of the present invention in a quantity in the range 0.0001% to 20% by weight of dry matter, with respect to the total cosmetic composition weight, more advantageously in the range 0.0005% to 10%, still more advantageously in the range 0.001% to 5%, in particular in the range 0.002% to 0.006%.

Advantageously, the cosmetic composition for topical administration of the present invention comprises at least one other ingredient of cosmetic interest selected from;
 a filling agent;
 a tightening agent;
 a hydrating agent.

In a tenth embodiment, the present invention further concerns a cosmetic care method for filling depressions in the skin, in particular wrinkles and/or fine lines, in particular at the surface of the skin and/or the mucous membranes, and/or to fill out the epidermis and/or to smooth the contours of the skin, and/or to plump the epidermis, and/or to improve hydration of the skin and/or the mucous membranes and/or the elasticity of the skin and/or the mucous membranes, and/or to encapsulate active agents of cosmetic and/or dermatological interest, and/or to prevent and/or treat the appearance of wrinkles in the epidermis, in particular superficial wrinkles, comprising administration, preferably by topical application, of at least one sphere in accordance with the present invention and/or a polymer in accordance with the fifth embodiment, or a cosmetic composition in accordance with the present invention.

In addition, in an eleventh embodiment, the present invention concerns a process for synthesizing spheres in accordance with the present invention, comprising the following steps:
 a) producing an emulsion:
  between at least a first phase, advantageously polar, comprising at least one hyaluronate compound and at least one glucomannan compound, said compounds being soluble in said first phase;
  and at least one second phase that is not miscible with the first phase and which is advantageously apolar;
 b) cross-linking said compounds in the presence of at least one cross-linking agent, said cross-linking agent being soluble in said second phase;
 c) recovering spheres;
 d) preferably, drying the spheres.

Advantageously, the hyaluronate compound has a low molecular weight, advantageously in the range 5 kDa to 200 kDa, preferably in the range 10 kDa to 40 kDa.

Advantageously, the cross-linking agent is terephthalic acid dichloride.

In particular in the context of the process of the present invention, the first phase is an aqueous phase and the second phase is an oily phase of fatty acid esters.

In a twelfth embodiment, the process in accordance with the present invention is such that the concentration of glucomannan in the first phase is in the range 0.1% to 5% by weight of dry matter with respect to the total weight of said first phase.

Advantageously, the concentration of hyaluronate compound of the first phase is in the range 0.1% to 25% by weight of dry matter with respect to the total weight of said first phase, preferably in the range 1% to 15%.

Advantageously, the ratio between the hyaluronate compound and the glucomannan compound in the first phase is in the range 75%/25% to 99%/1%, preferably in the range 90%/10% to 99%/1%; in particular, it is 98%/2%, by weight of dry matter.

In particular, the hyaluronate compound and the glucomannan compound together represent 0.2% to 30% by weight of dry matter of the first phase, preferably 2% to 20%.

A thirteenth embodiment of the process of the present invention is characterized in that the cross-linking agent is present in the second phase in a concentration by weight in the range 1% to 10% with respect to the total weight of the second phase.

Advantageously, the proportions by weight of cross-linking agent with respect to the weight of the whole constituted by the hyaluronate compound and the glucomannan compound are in the range 10% to 80%, but preferably in the range 10% to 40%.

In a fourteenth embodiment, the process of the present invention is characterized in that the period over which the cross-linking step b) is carried out is in the range 15 min to 24 h, preferably in the range 30 min to 90 min.

In a fifteenth embodiment, the process of the present invention is characterized in that in addition, it comprises at least one step for washing the spheres between steps b) and c) or after step c).

In a sixteenth embodiment, the process of the present invention is characterized in that in addition, it comprises at least one step for separation of the spheres between steps b) and c) or after step c).

In a seventeenth embodiment, the process of the present invention is characterized in that in addition, it comprises at least one step for drying the spheres between steps b) and c) or after step c).

Finally, the present invention concerns spheres, characterized in that they are obtainable by the process of the present invention.

Thus, the present invention pertains to spheres comprising at least one polymer of hyaluronate and glucomannan.

In accordance with the invention, the term "polymer of hyaluronate and glucomannan" means a molecule comprising at least one hyaluronate group and at least one glucomannan group, said groups being cross-linked, i.e. bonded together in a covalent manner, optionally via a group originating from the cross-linking agent.

Preferably, the polymer of hyaluronate and glucomannan is constituted by at least one hyaluronate group, and at least one glucomannan group cross-linked by a group originating from the cross-linking agent.

In the context of the present invention, the term "cross-linked" means having covalent bonds between the groups, possibly via a group originating from the cross-linking agent.

In a particularly advantageous embodiment, the hyaluronate group is cross-linked with the glucomannan group via ester type bonds, thereby forming a polyester polymer. Thus, advantageously, in the polymer, each bond between a hyaluronate group and a glucomannan group comprises at least one ester bond, preferably two ester bonds.

Advantageously, the hyaluronate compound is then cross-linked with the glucomannan compound, at at least one of their alcohol groups and/or carboxylic acid groups, preferably primary alcohols.

The polymer of hyaluronate and glucomannan of the invention is obtainable, and in particular is obtained, by cross-linking between a hyaluronate compound and a glucomannan compound using processes that are known to the skilled person.

Preferably, the polymer of hyaluronate and glucomannan is obtainable by interfacial cross-linking polymerization; advantageously, it is obtained by interfacial cross-linking polymerization between a hyaluronate compound and a glucomannan compound, preferably using a water-in-oil type emulsion. Advantageously, the cross-linking agent used for interfacial cross-linking is terephthalic acid dichloride.

Hyaluronic acid is a polymer of disaccharides composed of D-glucuronic acid and D-N-acetylglucosamine bonded alternately via β1-4 and β1-3 glycoside bonds. The presence of many hydroxyl groups, preferably primary alcohol functions, favors chemical reactions such as polymerizations, advantageously with the aid of an acid dichloride.

Hyaluronic acid or sodium hyaluronate has formula:

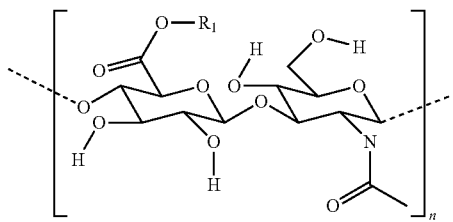

in which R1 denotes a hydrogen molecule in the case of hyaluronic acid, or Na in the case of sodium hyaluronate, and n denotes a whole number of repetitions from 10 to 6000, preferably 10 to 200, preferably 20 to 80.

The hyaluronate group of the polymer of the invention is obtained from a hyaluronate compound.

In accordance with the invention, the term "hyaluronate compound" means a molecule, in particular a polymer, containing one or more hyaluronate groups, in particular hyaluronic acid and/or one of its salts and/or one of its derivatives, preferably esterified derivatives.

In the context of the present invention, the term "hyaluronic acid salts" means ionic compounds that result from neutralization of the acid form of hyaluronic acid by an ion, in particular inorganic, in particular sodium, magnesium, chloride, sulfate or calcium; preferably, it is sodium and/or calcium hyaluronate, in particular sodium hyaluronate.

In the context of the present invention, the term "esterified derivatives of hyaluronic acid" means any derivative obtained by simple or multiple esterification of a primary or secondary alcohol function or of an acid function of the hyaluronic acid, and having on the esterified portion a carbon chain containing 1 to 6 carbon atoms, advantageously a linear or branched alkyl chain.

In an advantageous embodiment, the hyaluronic acid derivatives are selected from derivatives that are in routine use in cosmetics or dermatology such as, for example, those selected from esterified derivatives, in particular ascorbyl hyaluronate, benzyl hyaluronate, propylene glycol hyaluronate, acetylated sodium hyaluronate, butyroyl sodium hyaluronate or hydroxypropyltrimonium hyaluronate.

The hyaluronic acid salts and derivatives that may be used in the context of the present invention are cosmetically and/or pharmaceutically acceptable salts or derivatives, preferably dermatologically acceptable. Advantageously, the hyaluronic acid salts are selected from hydrolyzed calcium hyaluronate, hydrolyzed sodium hyaluronate, calcium hyaluronate, potassium hyaluronate, sodium hyaluronate, sulfated sodium hyaluronate and mixtures thereof.

In accordance with the invention, the hyaluronic acid salts and derivatives must have at least one primary alcohol function.

In a preferred embodiment, the hyaluronate compound is sodium hyaluronate.

Preferably, in accordance with the present invention, the hyaluronate compound, preferably hyaluronic acid, its salts or derivatives, in particular esterified derivatives, have a molecular weight of 5 kDa to 3000 kDa, preferably a low molecular weight, advantageously from 5 kDa to 200 kDa, advantageously 5 kDa to 100 kDa, preferably between 10 kDa and 40 kDa. A molecular weight of 2 kDa corresponds, for example, to n=4 times the base disaccharide forming the hyaluronic acid.

Sodium hyaluronate is commercially available, in particular from Technidd Chemi-tech, Wuhan Fortuna Chemical, Dalian Chem Imp. and Exp. Group, Afine Chemicals Limited, Javenech SA, Falcon Trading International, Cactus Botanics, A&E Connock, Welding Pharma, Maprecos, Landy Enterprise Limited, Chandigarh Medical Corporation, Kartik Enterprises, and DSA Exports.

Preferably, the hyaluronate group of the invention is obtained from a low molecular weight hyaluronate compound. Thus, the hyaluronate group of the polymer is advantageously of low molecular weight.

In the context of the present invention, the term "low molecular weight hyaluronate compound" means a hyaluronate compound with a molecular weight in the range 5 kDa to 200 kDa, preferably in the range 5 kDa to 100 kDa, more preferably in the range 10 kDa to 40 kDa. Advantageously, the hyaluronate group of the polymer has a molecular weight in the range 5 kDa to 200 kDa, preferably in the range 5 kDa to 100 kDa, more preferably in the range 10 kDa to 40 kDa.

In fact, as will be seen in Example 4, the Applicant has demonstrated that, even in the absence of glucomannan, microspheres of low molecular weight hyaluronate have higher efficacy than that of high molecular weight microspheres, in particular Filling Spheres™ hyaluronic. In combination with glucomannan, i.e. for the microspheres of the invention, the Applicant has shown, surprisingly, that this efficacy is improved still further.

Glucomannan is a polysaccharide with a high molecular weight. It is constituted by a principal chain formed solely by a β1-4 glycoside bond between D-glucose and D-mannose. Its molecular weight is in the range 200 to 2000 kDa. The presence of many hydroxyl groups, preferentially primary alcohol functions, favors chemical reactions such as polymerizations, in particular with the aid of an acid dichloride.

Konjac glucomannan has formula:

The glucomannan group is obtained from a glucomannan compound.

The term "glucomannan compound" as used in the invention is a compound that contains one or more glucomannan groups. In particular, it refers to konjac glucomannan, i.e. extracted from konjac root (*Amorphallus konjac*), such as those that are commercially available with the names Nutricol™, (FMC Corporation), Propol™ (SHIMITZU) or from Azelis, Baoji, Kalys and Novotech Nutraceuticals. However, glucomannan is also widespread, as a component of the cell wall of a wide variety of plants, yeasts, algae and fungi. Glucomannan may also be synthesized enzymatically in vitro. Preferably, in accordance with the present invention, the glucomannan group will be of natural origin and preferably obtained from konjac glucomannan or one of its derivatives.

The compound glucomannan may also be a derivative of glucomannan, preferably an esterified derivative, having at least one primary alcohol function.

In the context of the present invention, the term "esterified derivatives of glucomannan" means any derivative obtained by simple or multiple esterification of a primary or secondary alcohol function or of an acid function of glucomannan, and having, on its esterified portion, a carbon chain containing 1 to 6 carbon atoms, advantageously a linear or branched alkyl chain. In accordance with the invention, the glucomannan derivative must have at least one primary alcohol function.

Advantageously, the glucomannan group of the compound of the invention has a molecular weight in the range 100 kDa to 3000 kDa, preferably 200 kDa to 2000 kDa, more preferably 500 kDa to 1500 kDa. The glucomannan group of the polymer thus advantageously has a molecular weight in the range 100 to 3000 kDa, preferably 200 kDa to 2000 kDa, more preferably 500 to 1500 kDa.

In accordance with the invention, the molecular weights of the polysaccharides are preferably expressed as the weight average molecular weight: $\dot{M}_w$.

The polymer of the invention may be obtained by polymerization starting from a glucomannan compound and a hyaluronate compound. Preferably, it is obtained by interfacial cross-linking polymerization, preferably using an emulsion. This results in the formation of spheres in accordance with the invention.

The spheres of the invention may thus be obtained by cross-linking, starting from a glucomannan compound and from a hyaluronate compound, preferably by interfacial

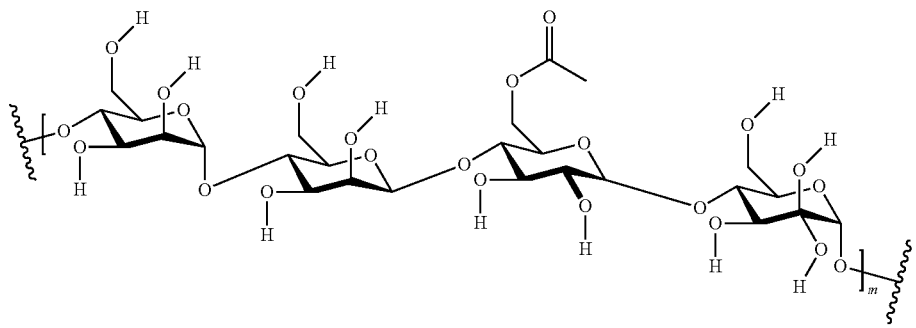

in which m is a whole number in the range 100 to 6000, preferably 200 to 3000, more preferably in the range 1000 to 2500.

cross-linking polymerization. Preferably, they are obtained by interfacial cross-linking starting from sodium hyaluronate and konjac glucomannan, more preferably in emulsion.

In fact, the spheres obtained thereby are particularly resistant and are thus easier to dehydrate. In addition, this process is particularly simple to carry out.

In the context of the present invention, the term "interfacial emulsion cross-linking" means a process that consists of producing an emulsion between two non-miscible phases, the first comprising at least one dissolved glucomannan compound and at least one dissolved hyaluronate compound, which are capable of reacting with at least one cross-linking agent dissolved in the other phase. Preferably, the cross-linking is carried out in water-in-oil emulsion, preferably as described in Example 1.

In the context of the present invention, the term "cross-linking agent" means a chemical compound that is capable of cross-linking the hyaluronate compound with the glucomannan compound, i.e. comprising at least two reactive functions.

Preferably, the cross-linking agent of the invention is capable of forming covalent ester type bonds with the glucomannan compound and the hyaluronate compound, preferably with an alcohol function and/or a carboxylic acid function, preferably primary or secondary alcohol, more preferably a primary alcohol of said compounds.

Preferably, the cross-linking agent of the invention is selected from an acid dichloride and/or an acid dianhydride, preferably selected from: terephthalic acid dichloride, phthalic acid dichloride, sebacic acid dichloride, succinic acid dichloride, fumaric acid dichloride, glutaric acid dichloride, oxalic acid dichloride, malonic acid dichloride, adipic acid dichloride, pimelic acid dichloride, azelaic acid dichloride, dodecanoic acid dichloride, undecanoic acid dichloride, the dichloride or trichloride of a tricarboxylic acid such as citric acid and/or an acid dianhydride such as succinic dianhydride, or one of their mixtures.

More preferably, the cross-linking agent is an acid dichloride, preferably selected from: terephthalic, sebacic, succinic and fumaric acid dichloride, or one of their mixtures.

Thus, the polymer of the invention preferably has the formula:

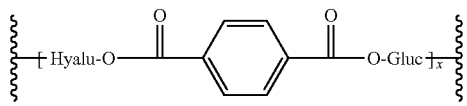

in which:
R2 represents a group deriving from the cross-linking agent, preferably the phthalate, terephthalate, sebacate, succinate, fumarate, glutarate, oxalate, malonate, adipate, pimelate, azelate, dodecanoate, undecanoate or tricarboxylate;
Hyalu represents a hyaluronate group, in particular deriving from sodium hyaluronate;
Gluc represents a glucomannan group;
and x is a whole number, preferably such that:
the hyaluronate group (Hyalu) represents 50% to 90%, more preferably 60% to 80% by weight of dry matter of the polymer of the invention;
the glucomannan group (Gluc) represents 1% to 10%, more preferably 1% to 5% by weight of dry matter of the polymer of the invention;
the group obtained from the cross-linking agent represents 10% to 40%, more preferably 20% to 30% by weight of dry matter of the polymer of the invention.

More preferably, the cross-linking agent of the invention is terephthalic acid dichloride.

Preferably, the interfacial cross-linking in accordance with the invention comprises the following steps:
a) producing an emulsion:
between at least a first phase, advantageously polar, comprising at least one hyaluronate compound, in particular of low molecular weight and at least one glucomannan compound, said compounds being soluble in said first phase;
and at least one second phase that is not miscible with the first phase and which is advantageously apolar;
b) cross-linking said compounds in the presence of at least one cross-linking agent, said cross-linking agent being soluble in said second phase;
c) recovering spheres, preferably by centrifuging.

The process may also include the following optional steps that may succeed step b) and c):
d) preferably, washing;
e) preferably, drying of the spheres obtained thereby.

The emulsion of the invention is preferably a water-in-oil type emulsion. In this case, the first phase is preferably an aqueous phase and the second phase is an oily phase, in particular of oily fatty acid esters and/or vegetable oils and/or mineral oils and/or silicone oils, preferably of fatty acid esters.

In a particular embodiment, the cross-linking agent is present in the second phase when step a) is being carried out. However, the cross-linking agent is preferably added in step b), i.e. once the emulsion has been formed. It is preferably added in the dissolved form in a solution that is miscible with the second phase, preferably in an oily solution, preferably a solution of fatty acid esters and/or vegetable or mineral oils and/or silicones oils, preferably of fatty acid esters.

Advantageously, the concentration of glucomannan compound in the first phase is in the range 0.1% to 5% by weight of dry matter with respect to the total weight of said first phase. Advantageously, the concentration of hyaluronate compound of the first phase is in the range 0.1% to 25% by weight of dry matter with respect to the total weight of said first phase, preferably in the range 1% to 15%.

Advantageously, the ratio between the hyaluronate compound and the glucomannan compound in the first phase is in the range 75%/25% to 99%/1% of dry matter, preferably in the range 90%/10% to 99%/1%; in particular, it is 98%/2%.

Advantageously, the hyaluronate compound and the glucomannan compound together represent 0.2% to 30% by weight of dry matter with respect to the total weight of said first phase, preferably 2% to 20%.

Advantageously, the first phase additionally comprises a buffer, preferably a carbonate buffer or a phosphate buffer.

Advantageously, the first phase is an alkaline aqueous phase, i.e. with a pH of more than 7, preferably in the range 7.1 to 10, preferably in the range 7.5 to 9.5.

Advantageously, the second phase additionally comprises an emulsifying agent, such as commercial products, for example "SPAN™", "TWEEN™", "BRIJ™" OR "ARLACEL™" products, but preferably, sorbitan trioleate is used, preferably in a concentration in the range 0.5% to 10% by weight with respect to the total weight of the second phase, preferably 1% to 5%.

Advantageously, the chemical cross-linking agent, preferably terephthalic acid dichloride, is present in the second phase in a concentration by weight in the range 1% to 10% with respect to the total weight of the second phase.

Advantageously, the proportions by weight of cross-linking agent to be used with respect to the weight of the unity constituted by the hyaluronate compound and the glucomannan compound is in the range 10% to 80% by weight of dry matter, preferably in the range 10% to 40%.

The cross-linking period may vary widely and depend on the starting material used, the cross-linking agent, the nature of the phases and the desired dimensions of the spheres, as is well known to the skilled person. This cross-linking period generally varies between 15 min and 24 h, preferably in the range 30 min to 90 min.

Advantageously, the emulsion is stirred, in particular to allow the formation of a sufficient quantity of the polymer of the invention.

The dimension of the spheres may be modified by adjusting the stirring rate during interfacial cross-linking, as is well known to the skilled person.

Advantageously, the process of the invention is carried out at a temperature that does not exceed 80° C.

Advantageously, the process of the invention also comprises a step for separating the spheres of the invention by any means known to the skilled person, such as decanting, but preferably by centrifuging or by filtration.

Advantageously, the process of the invention comprises one or more steps for washing the spheres in order to eliminate the reaction residues contained in one or the other of the phases, using a solvent that is miscible in one or the other of the phases, using techniques that are known to the skilled person.

Advantageously, the spheres of the invention are in the dehydrated form.

Advantageously, the process of the invention thus comprises one or more steps for drying the spheres, using techniques that are known to the skilled person, such as drying by conduction (rotary drum or cylinder dryers), by convection (rotary drum, fluidized bed dryers), by spray drying, or by zeodration, but preferably by lyophilization.

In a particular variation, it is then also possible to place the spheres in suspension in an appropriate vehicle, i.e. a vehicle that is preferably an anhydrous solvent and/or contains an apolar solvent in an amount of at least 10% of the total vehicle weight, preferably at least 20% of the total vehicle weight, and/or that has a total water content of less than 30% of the vehicle weight, preferably a silicone phase or an oily phase, preferably a solution of fatty acid esters, a mineral oil, a silicone, a wax, preferably a vegetable oil, preferably ethylhexyl palmitate.

In another particular variation, one of the phases, preferably the hydrophilic phase, comprises another ingredient, in particular of cosmetic or dermatological interest, in particular as defined below. This ingredient of cosmetic or dermatological interest will then be encapsulated inside the spheres of the invention.

When the active principle is liposoluble, it is possible to use in addition an emulsion stabilizing agent such as a colloid, a macromolecule or a synthetic or natural emulsifying agent.

The polymer may also be obtained using other conventional polymerization techniques such as interfacial cross-linking (without emulsion) or by polycondensation by esterification, i.e. by reacting a dibasic carboxylic acid or one of its derivatives such as an acid dianhydride, with a diol, producing the ester and another compound (water, carboxylic acid, etc.).

It is also possible to synthesize the polymer of the invention using conventional polyester synthesis techniques, starting from:
hydroxy acids such as α-hydroxy acids; the polymerization is also a polycondensation;
di-esters and dials; the technique is known as transesterification polycondensation;
lactones or cyclic diesters (glycolide, lactide, etc.): the polymerization then takes place by ring opening.

The spheres may also be obtained by dispersion using known techniques such as:
prilling, i.e. producing droplets from a needle or an injector, in particular from an electrostatic generator, by resonance (vibrational waves), by jet breaking and/or by a rotating disk;
by nebulization, i.e. producing droplets by passage through an air/liquid nozzle or by flowing over a disk rotating at high velocity;
by liquid/liquid emulsion, in particular by mechanical dispersion by stirring with a turbine or paddle reactor or by continuous dispersion using a static mixer;
by microemulsion or microdispersion.

The spheres may then be obtained by interfacial polymerization emulsion, in particular as described above, by dispersion or emulsion polymerization, i.e. by polymerization of the monomers in droplets of the emulsion in the presence of a cross-linking agent that is soluble in the droplets, in situ polymerization.

The spheres may also be obtained by starting from a polymer obtained by interfacial cross-linking without an emulsion, recovering then milling the polymer such as by ball milling, jet milling or cryogenic spraying, optionally with a spheronization step.

Advantageously, the polymer of hyaluronate and glucomannan represents at least 50% of the weight of dry matter of the spheres of the invention, preferably 60% to 90%.

Analysis by $^{13}C$ NMR of a polymer in accordance with the invention with formula:

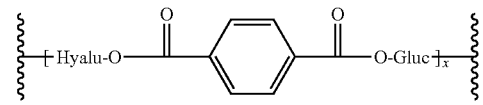

and preferably obtained in accordance with Example 1, has revealed that:
the hyaluronate group (Hyalu) represents 50% to 90%, more preferably 60% to 80% by weight of dry matter of the polymer of the invention;
the glucomannan group (Gluc) represents 1% to 10%, more preferably 1% to 5% by weight of dry matter of the polymer of the invention;
the group originating from the cross-linking agent, preferably the terephthalate, represents 10% to 40%, more preferably 20% to 30% by weight of dry matter of the polymer of the invention.

In a preferred embodiment, the spheres of the invention are microspheres. In fact, they are particularly suited to the cosmetic and dermatological uses of the invention since their shape and size means that they can penetrate into the epidermis and can be positioned ideally and at depth in the depressions of the skin, but without penetrating the dermis.

In the context of the present invention, the term "microspheres" means spheres with a diameter of 1 μm to 1000 μm. Advantageously, the microspheres of the invention have a diameter in the range 1 μm to 300 μm, more preferably 3 μm to 80 μm and in particular 3 μm to 20 μm. The term "diameter" preferably denotes the D50 diameter, more preferably the D90 diameter as measured conventionally by granulometry, in particular by laser diffraction using a MASTERSIZER 3000™ (Malvern) apparatus.

In the invention, the term "microspheres" also includes microcapsules.

In the context of the present invention, the term "microcapsules" means microspheres that include a wall. In this case, it is said wall that comprises the polymer of hyaluronate and glucomannan. The microcapsules are preferably obtained by interfacial cross-linking polymerization emulsion in a hydrophobic type solvent, in particular oil-in-water.

Preferably, the spheres, preferably the microspheres, are formed by the polymer of hyaluronate and glucomannan; more preferably, they are constituted by said polymer, optionally in combination with another cosmetic ingredient encapsulated inside the spheres or capsules and/or in the wall of the capsules.

Preferably, the spheres of the invention, preferably microspheres, are dehydrated.

In the context of the present invention, the term "dehydrated spheres" means spheres, preferably microspheres, with a water content of 0.1% to 50%, preferably 1% to 20%, more preferably 3% to 15% by weight.

The water content may be measured using known techniques, in particular using the Karl Fisher method as described in AFNOR standard T70-300 (December 2007). The water content may also be measured by measuring the loss on drying, corresponding to the measured adsorbed water. Preferably, the water content in the present invention is measured by the Karl Fisher method.

In fact, in the dehydrated form, the spheres of the invention, preferably microspheres, have better filling out capacities and thus have better activity.

The invention also pertains to a cosmetic or dermatological use, in particular as an agent for filling the surface of the epidermis and/or for mechanical filling out, preferably in the epidermis and/or as a hydrating agent, of at least a polymer and/or a sphere of the invention, in particular a low molecular weight polymer of hyaluronate and glucomannan obtained by crosslinking, preferably by an acid dichloride, preferably terephthalic.

The water sorption and swelling capacity of the polymers and/or spheres of the invention is ideally suited to cosmetic use for smoothing the contours of the skin, especially when the skin has a heterogeneous and/or rough appearance that is frequently inesthetic and disagreeable to the touch. This property of smoothing the contours of the skin is particularly advantageous in the context of makeup, so that the makeup can adhere better to the skin and/or to the mucous membranes.

Their great efficacy also makes the polymers and/or spheres of the invention particularly suited to cosmetic use as an agent for filling the surface of the epidermis, in particular when the skin has cutaneous depressions.

The term "cutaneous depressions" as used in the context of the invention means depressions, in particular those that are visible on the surface of the skin, in particular furrows linked to the appearance of fine lines and/or wrinkles. Furrows of 0.2 to 1 millimeter are considered to be fine lines. When they exceed 1 millimeter in depth, they are considered to be wrinkles. Fine lines and/or wrinkles preferentially appear at the nasolabial folds, the periorbital zone, the contour of the lips, or the forehead (glabellar lines). Skin depressions also include other types of visible depressions such as scar depressions, in particular those brought about by acne.

The term "agent for filling the surface of the epidermis" as used in the invention means an agent that is capable of filling superficial skin depressions, i.e. capable of causing, at the surface of the skin and/or the mucous membranes, a measurable reduction in the depth of one or another of these skin depressions, in particular the depth of furrows linked to the appearance of fine lines and/or wrinkles, in particular to fill them up.

The term "filling out agent" as used in the present invention means an agent that is capable of increasing in volume on contact with water. This increase may in particular be measured as described in Example 4.

The term "epidermal filling out agent" as used in the present invention means a filling out agent that is capable of penetrating the epidermis and, in contact with water, of increasing the volume and thus the thickness of the epidermis.

Thus, as shown in particular in Example 5, the polymers and spheres of the invention can be used to swell the volume of the epidermis, in particular of the stratum corneum, and thus of increasing the thickness of the epidermis. The polymers and/or spheres of the invention are thus also ideally suited to use for young to old skin and/or mucous membranes, for individuals wishing to fill out the epidermis of certain zones of their face for esthetic reasons (plumping), for example to plump the epidermis of the lips, in particular of thin lips, and/or to plump the epidermis of the cheeks, in particular the apples of the cheeks.

The term "plump" as used in the invention means to visibly increase the size and/or volume and/or thickness of the epidermis in the zone under consideration.

Further, by capturing and retaining water in the skin and/or the mucous membranes, the polymers and/or the spheres of the invention participate in increasing the degree of hydration of the cutaneous tissue, thus meaning that skin and/or mucous membrane hydration can be improved.

In the context of the present invention, the term "to improve hydration of the skin and/or the mucous membranes" means preventing and/or combatting the loss of water in the skin and/or the mucous membranes, and/or increasing its water content.

This improvement to hydration of the skin and/or the mucous membranes results in an improvement in their viscoelastic properties, in particular their suppleness, firmness and elasticity.

Thus, the invention pertains in particular to a cosmetic use of at least one polymer in accordance with the invention, in particular a polymer of hyaluronate and glucomannan, preferably cross-linked by means of at least one ester bond, preferably a low molecular weight hyaluronate, more preferably cross-linked by an acid dichloride, preferably terephthalic, or spheres of the invention as an agent for filling out the epidermis and/or an agent for filling the surface of the epidermis and/or for smoothing the contours of the skin, and/or for plumping the epidermis and/or for improving hydration of the skin and/or the mucous membranes and/or the viscoelastic properties of the epidermis of the skin and/or the mucous membranes, and/or to encapsulate another ingredient of cosmetic interest, and/or to prevent and/or treat the appearance of wrinkles in the epidermis.

The polymer and/or the sphere of the invention are preferably used alone, in particular in the dehydrated, in particular lyophilized form, or in the form of a mixture of cosmetic ingredients contained in a cosmetic and/or dermatological vehicle appropriate to its formulation and/or to its integration into a cosmetic composition. The polymer and/or the sphere of the invention may also be used in a cosmetic or dermatological composition, i.e. in combination with an appropriate cosmetic or dermatological vehicle, preferably for topical application.

The present invention also pertains to a cosmetic composition for topical administration, preferably to a human being, comprising the polymer of the present invention and/or spheres in accordance with the invention, in particular for one or other of the uses cited above, in an appropriate cosmetic or dermatological vehicle.

The term "appropriate cosmetic or dermatological vehicle" as used in the present invention means a solvent containing at least one apolar solvent in a minimum content of 10% by weight with respect to the total composition weight, preferably 20% by weight, preferably a solution of fatty acid esters, a mineral oil, a silicone, a wax, preferably a vegetable oil, preferably ethylhexyl palmitate.

Advantageously, the vehicle also comprises an oil texturing agent, preferably trihydroxystearin, a mixture of mineral oil and dibutyl glutamide lauryl, disteardimonium hectorite, stearalkonium hectorite, in particular mixed with propylene carbonate and caprylic/capric triglycerides and/or isopropyl myristate and/or octylpalmitate, trihydroxystearin, silica gel, dibutylhexanoyl or dibutyllauroyl glutamide, polyethylene, or polyalphaolefins, more preferably trihydroxystearin.

Advantageously, the polymer and/or the spheres of the present invention are included in the composition in a quantity in the range 0.0001% to 20% by weight of dry matter, with respect to the total cosmetic or dermatological composition weight, more advantageously in the range 0.0005% to 10%, still more advantageously in the range 0.001% to 5%, in particular in the range 0.001% to 0.01%, more particularly in the range 0.002% to 0.006% of the total composition weight. The cosmetic composition preferably also contains a cosmetic vehicle and/or excipient.

Advantageously, the cosmetic compositions of the invention contain other ingredients of interest, in particular cosmetic ingredients, preferably agents with complementary properties. Preferably, they are conventional ingredients in anti-aging and/or hydrating compositions, and/or ingredients for improving the visco-elastic properties of the skin and/or the mucous membranes, in particular those selected from filling agents, tightening agents, hydrating agents, agents stimulating the molecules of the extracellular matrix, fibroblast growth factor (FGF) protecting agents, or agents stimulating the activity and/or proliferation of fibroblasts.

In accordance with an advantageous embodiment, the cosmetic compositions of the invention contain at least one ingredient of interest, in particular cosmetic, selected from the group constituted by:

- a filling agent, such as those sold by the Applicant with the trade name MARINE FILLING SPHERES™, FILLING SPHERES™ hyaluronic, HYALUROSMOOTH™ [HYALUPULP veg spheres (for l'OREAL)], or those sold with the name SYM3D™ (Symrise); EFFIPULP™ (Expanscience); HYADISINE™ (Lipotech); HILURLIP™ (Lipotech);
- a tightening agent, such as those sold by the Applicant with the name QUICKLIFT™;
- a hydrating, emollient or wetting agent leading to a complementary or possibly synergistic effect, in particular to reinforce the barrier function and reduce insensible water losses and/or those that increase the water content of the skin and/or the mucous membranes or stimulate secretory activity of sebaceous glands and/or stimulate the synthesis of aquaporin to improve the circulation of water in the cells. Non-limiting examples of active ingredients that may be cited are as follows: trehalose, serine, urea and mixtures thereof; other spheres sold with the name MARINE FILLING SPHERES™, ADVANCES MOISTURIZING COMPLEX™, HYALURONIC FILLING SPHERES™, VEGETAL FILLING SPHERES™, OSMOGELLINE™, MICROPATCH™, alkylcelluloses, lecithins, sphingoid-based compounds, ceramides, phospholipids, cholesterol and its derivatives, glycosphingolipids, phytosterols (stigmasterol and beta-sitosterol, campesterol), essential fatty acids, 1-2 diacylglycerol, 4-chromanone, pentacyclic triterpenes such as ursolic acid, vaseline, lanolin, sugars, in particular trehalose and its derivatives, rhamnose, fructose, maltose, lactose, erythritol, mannitol, D-xylose and glucose, adenosine and its derivatives, sorbitol, polyhydric alcohols, advantageously C2-C6, and more advantageously C3-C6, such as glycerin, propylene glycol, 1,3-butylene glycol, dipropylene glycol, diglycerin, polyglycerin and their mixtures, glycerol and its derivatives, glycerol polyacrylate, sodium lactate, pentanediol, serine, lactic acids, AHAs; preferably trehalose, serine, urea and/or mixtures thereof;
- an agent stimulating the synthesis of molecules of the extracellular matrix, in particular glycoaminoglycans (GAG) and/or elastin and/or collagen such as retinol, vitamin C and their derivatives, for example, tetrapeptides containing 50 to 500 ppm of palmitoyl-Gly-Gln-pro-Arg, such as those sold with the name Matrixyl™ by Sederma, or a mixture of plant extracts sold with the name STRIVECTIN™, or compounds containing them;
- a hydrating agent, in particular an agent stimulating the synthesis of lipids such as, for example, a biotechnologically-modified yeast extract sold by the Applicant with the name RELIPIDIUM™;
- a fibroblast growth factor (FGF) protective agent, in particular FGF2, such as the plant extract described in the Applicant's patent application GB244036, in particular an extract of Hibiscus abelmoscus, in particular that sold with the name LINEFACTOR™;
- an agent stimulating the activity and/or proliferation of fibroblasts, such as a fermented soy peptide extract sold with the name PHYTOKINE™, optionally in combination with an extract of Hibiscus abelmoscus sold with the name LINEFACTOR™, as described in the Applicant's patent application WO2009121422;
- an agent stimulating the activity and/or synthesis of a Lysyl Oxidase Like LOXL, in particular selected from the compounds described in patent application FR2855968, in particular an extract of dill (*Peucedanum graveolens*), to stimulate the elastic fibers;
- an anti-inflammatory agent, in particular inhibiting PLA2, in particular one of the active ingredients described in patent application FR2847267, preferably an extract of *Pueraria lobata* roots (INHIPASE™);
- a draining agent, especially hesperitin laurate (FLAVAGRUM™), or quercetin caprylate (FLAVENGER™);
- a dermal structure restoring agent such as an ursolic acid stabilized in a liposome, sold by the Applicant with the name URSOLISOME™;
- an anti-glycation agent, in particular those described in patent application WO2009007411, preferably *Davilla rugosa* extract;

an agent stimulating the synthesis of laminin, in particular a malt extract modified by biotechnology; such an extract is in particular sold by the Applicant with the name Basaline™;

an agent stimulating the expression and/or activity of hyaluronan synthase 2 (HAS2) such as the plant extracts described in patent application FR 2 893 252 A1, in particular an aqueous extract of Galanga (*Alpinia galanga*);

an agent mimicking the effects of beta-endorphins, such as those cited in patent application US 2006069032, a cocoa extract or an extract of *Tephrosia purpurea* (Soliance);

an agent stimulating the synthesis of fibronectin, in particular a maize extract, such an extract being sold by the Applicant with the name DELINER™;

an agent mimicking the effects of DHEA, in particular stimulating lipid synthesis, and preventing glycation, in particular an extract of mallow leaves (*Malva sylvestris*) sold by the Applicant with the name PHYSTROGENE™;

a slimming agent;

or one of their mixtures.

In an advantageous embodiment, at least one other ingredient, in particular of cosmetic interest, preferably selected from those defined above, is contained in the spheres of the invention and/or present in the wall of the capsules of the invention, and/or encapsulated inside spheres in accordance with the invention. In particular, it is a filling agent and/or a tightening agent and/or a hydrating agent.

The cosmetic compositions of the invention may contain an excipient such as, for example, at least one compound selected from the group consisting of preservatives, emollients, emulsifiers, surfactants, hydrating agents, thickening agents, conditioners, mattifying agents, stabilizers, antioxidants, texturing agents, shine-producing agents, film-forming agents, solubilizers, pigments, dyes, fragrances and sunscreens. These excipients are preferably selected from the group consisting of amino acids and their derivatives, polyglycerols, cellulose esters, polymers and derivatives, lanolin derivatives, phospholipids, lactoferrins, lactoperoxidases, sucrose-based stabilizers, E vitamins and their derivatives, natural and synthetic waxes, vegetable oils, triglycerides, unsaponifiables, phytosterols, plant esters, silicones and their derivatives, protein hydrolyzates, jojoba oil and its derivatives, lipo/hydrosoluble esters, betaines, aminoxides, plant extracts, saccharose esters, titanium dioxides, glycines, and parabens, and more preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerin, dihydroxycetyl sodium phosphate, isopropyl hydroxycetyl ether, glycol stearate, triisononanoin, octyl cocoate, polyacrylamide, isoparaffin, laureth-7, a carbomer, propylene glycol, glycerol, bisabolol, a dimethicone, sodium hydroxide, PEG 30-dipolyhydroxysterate, capric/caprylic triglycerides, cetearyl octanoate, dibutyl adipate, grapeseed oil, jojoba oil, magnesium sulfate, EDTA, a cyclomethicone, xanthan gum, citric acid, sodium lauryl sulfate, mineral waxes and oils, isostearyl isostearate, propylene glycol dipelargonate, propylene glycol isostearate, PEG 8, beeswax, hydrogenated palm kernel oil glycerides, hydrogenated palm oil glycerides, lanolin oil, sesame oil, cetyl lactate, lanolin alcohol, castor oil, titanium dioxide, lactose, saccharose, low density polyethylene or an isotonic salt solution.

Advantageously, the compositions cited above are formulated into a form selected from the group consisting of an aqueous or oily solution, a cream or an aqueous gel or an oily gel, in particular in a pot or tube, especially a shower gel, shampoo; a milk; an emulsion, a microemulsion or a nanoemulsion, in particular oil-in-water or water-in-oil or a multiple emulsion or silicone emulsion; a mask; a lotion, in particular in a glass, plastic or measuring bottle or as an aerosol; an ampoule; a liquid soap; a dermatological bar; a pomade; a foam; an anhydrous product, preferably liquid, paste or solid, for example in the form of a stick, especially in the form of a lipstick or pressed product.

In the present invention, the term "topical application" means application of the composition to the surface of the skin and/or the mucous membranes, in particular by direct application or by vaporization.

In accordance with the invention, the term "mucous membranes" is used to describe the buccal, labial, nasal, ocular, anal and/or urogenital mucous membranes, in particular ocular.

The terms "appropriate cosmetic or dermatological vehicle" used here means that the composition or the components thereof are suitable for use in contact with human skin and/or mucous membranes without undue toxicity, incompatibility, instability, allergic response, or their equivalents.

A number of cosmetically active ingredients are known to the skilled person for improving the health and/or physical appearance of the skin. The skilled person will know how to formulate the composition or dermatological compositions to obtain the best effects. On the other hand, the compounds described in the present invention may have a synergistic effect when they are combined with each other. These combinations are also covered by the present invention. The CTFA Cosmetic Ingredient Handbook, Second Edition (1992) describes various cosmetic and pharmaceutical ingredients in current use in the cosmetics and pharmaceuticals industry that are particularly suitable for topical use. Non-limiting examples of these classes of ingredients include the following: abrasives, adsorbents, compounds with an esthetic purpose such as fragrances; pigments; dyes; essential oils; astringents such as clove oil, menthol, camphor, *eucalyptus* oil, eugenol, menthyl lactate, witch hazel distillate; anti-acne agents; anti-flocculation agents; anti-foaming agents; antimicrobial agents such as iodopropyl butylcarbamate; antioxidants such as ascorbic acid; binders; biological additives; buffers; swelling agents; chelating agents; additives; biocidal agents; denaturing agents; thickening agents; and vitamins; film-forming materials; polymers; opacifying agents; pH adjusters; reducing agents; conditioning agents such as wetting agents, and derivatives or equivalents thereof.

The cosmetic compositions of the invention are preferably anti-age care products and/or lifting products and/or plumping products and/or hydrating products and/or tightening products and/or under-makeup primers.

The invention also pertains to a cosmetic care method comprising administration, preferably topical administration, of at least one polymer of the invention, in particular a polymer of hyaluronate and glucomannan, preferably cross-linked by interfacial cross-linking, preferably via terephthalic acid dichloride, optionally in the form of a cosmetic composition in accordance with the invention.

More particularly, the present invention provides a cosmetic care method for filling cutaneous depressions on the surface of the epidermis, in particular wrinkles and/or fine lines, and/or to smooth the contours of the skin, and/or to plump the epidermis and/or to improve skin and/or mucous membrane hydration and/or the elasticity of the skin and/or mucous membranes, and/or to smooth the epidermis of the skin and/or the mucous membranes, and/or to encapsulate and/or vectorize active agents, and/or to prevent and/or treat the appearance of wrinkles in the epidermis, in particular superficial wrinkles, comprising the administration, preferably topical administration, of at least one polymer and/or spheres in accordance with the invention, optionally in the form of a cosmetic composition in accordance with the invention.

More particularly, the compositions of the invention are applied to a portion of the human body showing signs of skin aging and/or likely to show signs of skin aging, in particular wrinkles and/or fine lines, in particular to the face, neck, neckline and/or the hands, in particular the nasolabial folds and/or the periorbital zone and/or the contour of the lips and/or the forehead (glabellar lines).

More particularly, the compositions of the invention are applied to the face, preferably daily, preferably once or twice a day, preferably morning and/or evening.

The compositions of the invention may also be dermatological, in particular for their use in the prevention and/or treatment of disorders involving a reduction in the water content of the epidermis, such as in the treatment and/or prevention of chaps and/or dartre or achromic seborrheic dermatitis and/or cracks and/or atopic dermatitis and/or ichthyosis and/or pathological skin and/or mucous membrane dryness accompanying skin pathologies and/or mucous membrane pathologies such as eczema.

The spheres and the polymer of the invention in the dehydrated forms are also useful in increasing water sorption properties, in particular absorption and/or adsorption of water from an adsorbent article such as diapers, sanitary towels, pads, incontinence products, or absorbent tissue and/or foam. The spheres and/or the polymer of the invention may, for example, be added to the lining of the article.

The spheres and the polymer of the invention in the dehydrated form are of particular use as a super-absorbent agent.

Other aims, features and advantages of the invention will become apparent to the skilled person from the following explanatory description that makes reference to the examples and to the figures which are given solely by way of illustration and which do not in any way limit the scope of the invention.

The examples form an integral part of the present invention; any feature that appears novel over any prior art from the description taken as a whole, including the examples, forms an integral part of the invention in its function and in its generality.

Thus, each example has a general scope.

Further, in the examples and unless indicated otherwise, the temperature is expressed in degrees Celsius and the pressure is the atmospheric pressure, unless indicated otherwise.

EXAMPLES

Example 1

Process for the Production of Spheres in Accordance with the Invention with Very Low Molecular Weight Sodium Hyaluronate (Comprised Between 10 and 40 kDa)

Microspheres were obtained by interfacial cross-linking polymerization starting from sodium hyaluronate and konjac glucomannan, in the presence of terephthalic acid dichloride as a cross-linking agent.

1) An aqueous solution of konjac glucomannan and sodium hyaluronate was prepared as follows: 10 g of low molecular weight sodium hyaluronate (with a weight average molecular weight in the range 10 to 40 kDa), 0.25 g of konjac glucomannan (with a molecular weight in the range 200 to 2000 kDa) and 4.8 g of sodium bicarbonate buffer were suspended in 100 g of demineralized water.
2) Preparation of emulsion: the aqueous solution produced in 1) was emulsified in an oily phase comprising 300 mL of hexyl laurate and 6 mL of sorbitan trioleate. Depending on the desired size for the spheres, stirring was carried out using a mechanical stirrer (size in the range 100 to 900 µm) or an ULTRA-TURAX™ (size in the range 5 to 100 µm), in this case with an ULTRA-TURAX™.
3) Cross-linking of formed spheres: an oily phase comprising 400 ml of hexyl laurate and 20 g of terephthalic acid dichloride was prepared with stirring. After dissolving the acid dichloride completely, the oily phase was added, with stirring, to the emulsion described in 2).

This was stirred for 90 min in order to bring about polymerization between the activated diacid on the one hand and the alcohol functions of the polysaccharides on the other hand. This reaction was favored in a basic medium (pH 8.6), and so relatively long reaction times were required before cross-linking was sufficient. Ten grams of polymer were obtained. The yield of the reaction is thus 100%.
4) Presentation of spheres: after reaction, the spheres were separated by decanting or by centrifuging, depending on their size. They were washed several times then dehydrated by lyophilization to a water content of 5% to 15%.
5) They were then suspended in an oil, for example in an amount of 0.2% by weight, then used as they were or with other cosmetic or dermatological ingredients.

The microspheres obtained are illustrated in FIG. 1. Their granulometry was measured by laser diffraction with the MASTERSIZER™3000 (Malvern) apparatus and the spheres had a D90 diameter of 39.01 µm.

Example 2

Process for the Production of Spheres in Accordance with the Invention with Low Molecular Weight Sodium Hyaluronate (Weight Average Molecular Weight=100 kDa)

The protocol of Example 1 was carried out in the same manner with an aqueous solution containing 6.8 g of low molecular weight sodium hyaluronate (molecular weight in average by weight of 100 kDa) at pH 8.66. The quantity of polymer obtained was 5.2 g. The yield of the reaction is thus of 69%.

Microspheres according to the invention were also obtained with low molecular weight sodium hyaluronate (weight average molecular weight=100 kDa), but compare to the ones obtained with very low molecular weight sodium hyaluronate (Example 1), the yield of the reaction was lower, thus being less interesting industrially. Moreover, the amount of solubilized sodium hyaluronate in the aqueous solution was lower.

Example 3

Production of Spheres of Glucomannan and High Molecular Weight Sodium Hyaluronate (Weight Average Molecular Weight: 1500 kDa-3000 kDa According to the Invention The protocol of Example 1 was carried out in the same manner with an aqueous solution containing 1 g of high molecular weight sodium hyaluronate (weight average molecular weight of 1500 kDa-3000 kDa) at pH 8,56.

The resulting process was very difficult to carry out and the spheres obtained were easily broken.

Comparative Example 1

Production of Spheres of Glucomannan Polymer

The protocol described in Example 1 was carried out in the same manner with an aqueous solution containing either 0.5 g of konjac glucomannan or 1 g of konjac glucomannan.

Microspheres based on glucomannan alone were obtained, showing evidence of cross-linking, but they were destroyed by the centrifuging, washing and dehydration steps.

Example 4

Study of the Water Absorption Capacity and Filling out Capacity of the Spheres of the Invention Principle:

This study was for the purposes of quantifying in vitro the swelling power of the spheres of the invention by measuring two parameters that could be used to evaluate the water absorption and filling out capacity:
- the quantity of water absorbed by 0.2 g of spheres;
- the degree of filling out, or the ratio of the volumes of the hydrated/dehydrated spheres, for 0.2 g of dehydrated spheres.

Protocol:

A quantity of 0.2 g of dehydrated spheres was introduced into a test tube that had been tared (Tare). The dry height (Hdry) of the settled powder was measured.

A quantity of 10 ml of distilled water was added using a syringe. The tube was stirred under vortex stirring (maximum speed). The spheres were allowed to fill out for approximately 1 h. Vortex stirring was carried out for homogenization, then the tube was centrifuged at 4000 rpm for 4 min. The excess water was sucked off. The quantity of water absorbed by the spheres (Qwater) was measured using the formula: Qwater=Mtot−Tare−0.2 in which Mtot=mass of tube+residue of hydrated spheres.

The height of the gel formed by the rehydrated spheres (Hwet) was measured.

The water absorption capacity corresponded to the ratio between Qwater and the mass of the dehydrated spheres (0.2 g).

The degree of filling out corresponded to the ratio between Hdry and Hwet.

The test was carried out 6 times.

The experiment was carried out for (i) 0.2 g of dehydrated spheres in accordance with the invention obtained in accordance with Example 1, (ii) 0.2 g of FILLING SPHERES™ hyaluronic and (iii) 0.2 g of dehydrated hyaluronate spheres without glucomannan, obtained with the same hyaluronate (10 g of sodium hyaluronate) as for the spheres of the invention using the protocol defined in Example 1 and known as HA spheres.

FILLING SPHERES™ hyaluronic are sold by the Applicant and are obtained from high molecular weight hyaluronate (250 kDa to 3 MDa) alone, by interfacial cross-linking using the process described in Example 1.

Results:

The results obtained are presented in Table 1 and in Table 2.

TABLE 1

| Quantity of water absorbed by 0.2 g of spheres | | |
|---|---|---|
|  | Qwater (g) | Water absorption capacity |
| Filling Spheres ™ hyaluronic | 3.49 +/− 0.15 | 17.5 |
| Spheres of the invention | 4.93 +/− 0.23 | 24.7** |

Mean ± standard deviation, n = 6
**statistically significant vs. FILLING SPHERES ™ hyaluronic, p < 0.01

Conclusion:

The polymers of the invention could absorb up to 24 times their weight of water; i.e. 1.4 times more than FILLING SPHERES™ hyaluronic.

TABLE 2

| Degree of filling out | | |
|---|---|---|
|  |  | Mean ± standard deviation |
| Filling Spheres ™ hyaluronic | Hwet (mm) | 33.33 ± 1.21 |
|  | Degree of filling out | 4.17 ± 0.15 |
|  | Hdry (mm) | 8 |
| HA spheres | Hwet (mm) | 48.17 ± 0.41 |
|  | Degree of filling out | 6.02 ± 0.05 |
|  | Hdry (mm) | 8 |
| Spheres of the invention | Hwet (mm) | 50.00 ± 2.10 |
|  | Degree of filling out | 16.67** ± 6.70 |
|  | Hdry (mm) | 3 |

Mean ± standard deviation, n = 6
**statistically significant vs. FILLING SPHERES ™ hyaluronic, p < 0.01

Conclusion:

The spheres of the present invention have a filling out power that is 4 times higher than that of FILLING SPHERES™ hyaluronic and 2.8 times higher than that of HA spheres, i.e. the spheres of the same hyaluronate polymer comprising no glucomannan Example 5

Absorption Capacity Measured by Dynamic Vapor Sorption

Principle:

This study was intended to quantify the water retention capacity of a polymer in vitro by monitoring the variation in the weight of the polymer over time at different relative humidities between 0 and 90%.

Protocol:

5 mg of spheres in the dehydrated form were introduced into a high performance thermobalance. The experiment was carried out with an inert gas (nitrogen), at 25° C. The chamber was pre-dried for 120 min at 60° C. at a relative humidity of 0%. Next, stages of humidity were programmed from 10% to 90% then 90% to 10%. An equilibration time of 120 min was allowed at each stage.

The experiment was carried out (i) for the spheres of the invention obtained in accordance with Example 1, and (ii) for the FILLING SPHERES™ hyaluronic.

Figure 2:
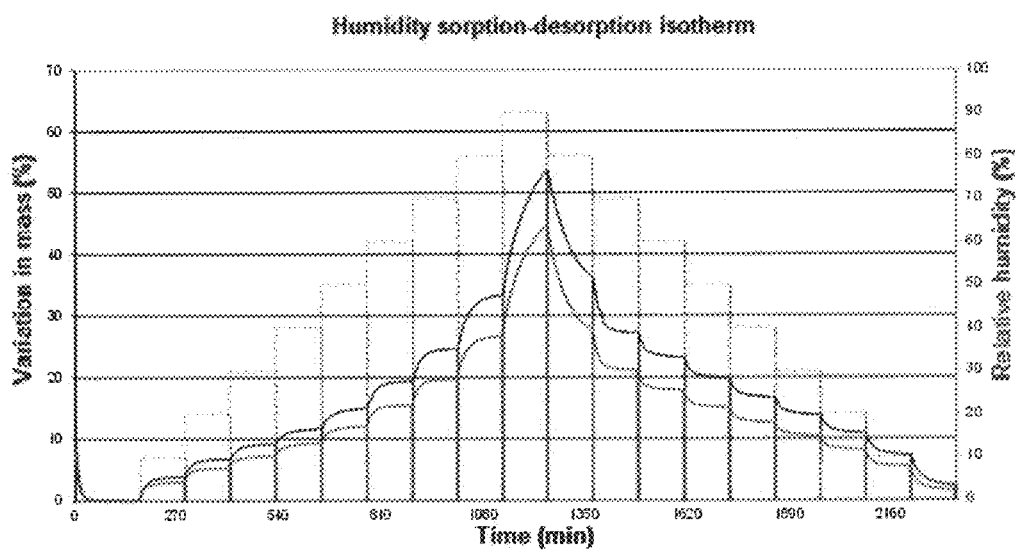
FIG. 2 represents the sorption-desorption isotherm (change of weight as a percentage and relative humidity as a %) as a function of time for the spheres of the invention and for prior art spheres (FILLING SPHERES™ hyaluronic spheres, based on hyaluronic acid alone)

Results:

The results obtained are presented in FIG. 2.

In the histogram representing the relative humidity, the highest curve represents the spheres of the invention, the lowest curve represents the FILLING SPHEREShk™ hyaluronic.

The graph of FIG. 2 shows that the spheres of the invention have a better water retention capacity than those composed of a polymer of hyaluronic acid cross-linked with a terephthalic acid dichloride.

At the maximum relative humidity point (90%), the value obtained by the microspheres of the polymer of the invention was 20% higher than that of the FILLING SPHERES™ hyaluronic polymer.

Example 6

Swelling of Stratum Corneum Using an Ex Vivo Test on Skin Biopsies

Aim:

To demonstrate the swelling power of the polymers of the invention by means of an ex vivo test on human biopsies, in particular that of the spheres obtained in accordance with Example 1, compared with FILLING SPHERES™ hyaluronic.

Principle:

Swelling of the stratum corneum was determined by measuring its thickness on histological sections of human skin.

A novel method of visualization as well as a quantitative evaluation of the changes in the thickness of the stratum corneum were used for this study.

Protocol:

The human biopsy was placed under normal relative humidity conditions (44%) for approximately 16 hours in order to equilibrate the skin.

The thickness of the stratum corneum, constituted by approximately 15 layers of cells, was evaluated after treating the skin with the spheres of the invention on the one hand, in particular as obtained in Example 1, and on the other hand with FILLING SPHERES™ hyaluronic, in an amount of 4 mg/cm$^2$ of skin.

The spheres of the invention and the FILLING SPHERES™ hyaluronic were each in the form of dehydrated spheres in suspension in an oily support (ethylhexyl palmitate) in an amount of 0.2%.

Treatment of the human biopsies with the two products was carried out for 4 hours, in a controlled atmosphere, namely in a relative humidity that was fixed at 44%.

At the end of the treatment, the biopsies were frozen and stored in liquid nitrogen. 10 µm sections were produced then prepared for observation in a TCS-SP2 confocal microscope. The thickness of the stratum corneum was observed for 10 sections per biopsy, with 5 measurements per section. The fluorescence was quantified using LEICA™ software.

The comparison between the spheres of the invention and the FILLING SPHERES™ hyaluronic was evaluated statistically using a Student t test (significance ***: $p<0.001$), over the means obtained for the measurement of the thickness of the stratum corneum.

Figures 3A, 3B:
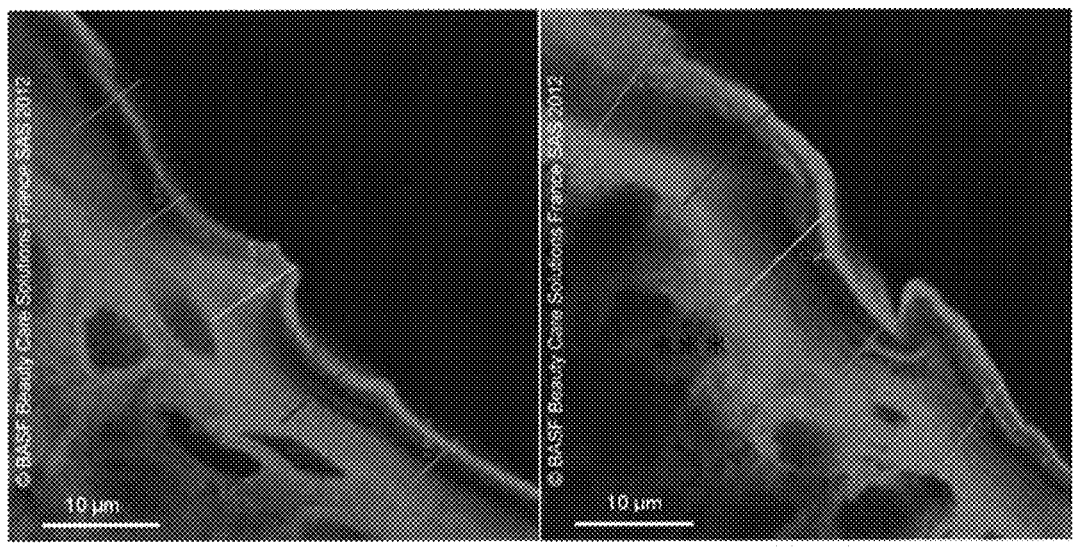
FIG. 3 represents a confocal microscopy image of a section of human skin treated with prior art FILLING SPHERES™ hyaluronic (FILLING SPHERES™ hyaluronic, based on hyaluronic acid alone) (FIG. 3a) and a biopsy treated with spheres in accordance with the invention obtained in Example 1 (FIG. 3b)

Results:

The results are presented in the table below and in FIGS. 3a and 3b: Mean±SD, n=50 ***. The results obtained for the spheres of the invention are statistically significant compared with the FILLING SPHERES™ hyaluronic, $p<0.001$.

|  | Filling Spheres™ hyaluronic | Spheres of the invention |
| --- | --- | --- |
| Mean thickness, stratum corneum | 8.38 +/− 0.46 | 9.83 +/− 0.50 |

-continued

|  | Filling Spheres™ hyaluronic | Spheres of the invention |
| --- | --- | --- |
| %/Filling Spheres™ hyaluronic |  | 17.30% |

Conclusions:

The results obtained with the treatment with the spheres of the invention show a swelling of the stratum corneum that was greater than that obtained with the treatment by the FILLING SPHERES™ hyaluronic. The efficacy of the spheres of the invention compared with the FILLING SPHERES™ hyaluronic was significant for this stratum corneum swelling test. Thus, the spheres of the invention can be used to thicken the stratum corneum by 17% more than that brought about by the FILLING SPHERES™ hyaluronic. This result is statistically significant ($p<0.0003$).

Example 7

Filling Out of Spheres by Optical Microscopy

Principle:

This study was intended to evaluate filling out of the FILLING SPHERES™ hyaluronic by optical microscopy. Image analysis software was used to calculate the surface area of the dehydrated spheres, then of the spheres in the rehydrated form. The filling out factor using this technique is defined as the ratio of the surface areas.

Figure 4:
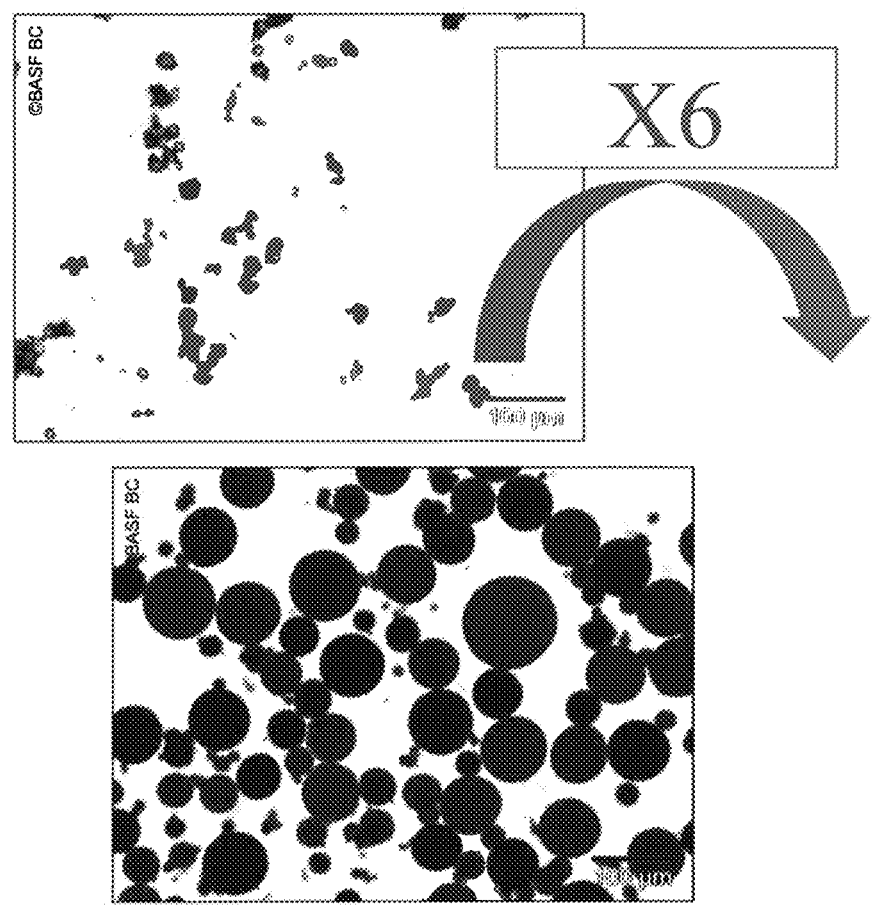
FIG. 4 represents optical microscopy photographs of filling out of the spheres of the invention obtained in Example 1 by a factor of 6 (X6): the top image represents the dehydrated spheres of the invention and the bottom image represents the spheres of the invention rehydrated using pure water and methylene blue.

Results and Discussion:

When the spheres of the invention are observed under the optical microscope in their dehydrated form, they appear small and dense. After rehydration, they appeared to be more voluminous and very round. The surfaces of each form of the spheres were analyzed by the image processing software (FIG. 4).

The filling out factor obtained thereby was ×6.

Conclusion:—

The optical microscopy technique confirmed the exceptional filling out behavior of the spheres of the invention in contact with water.

Example 8

Nuclear Magnetic Resonance Study of Polymer of the Invention

Principle:

A carbon 13 ($^{13}$C) NMR analysis was carried out in order to identify the carbon atoms in the polymer of the invention.

Protocol:

The spheres obtained in the dry form in accordance with Example 1 were analyzed by carbon 13 NMR.

Figure 5:
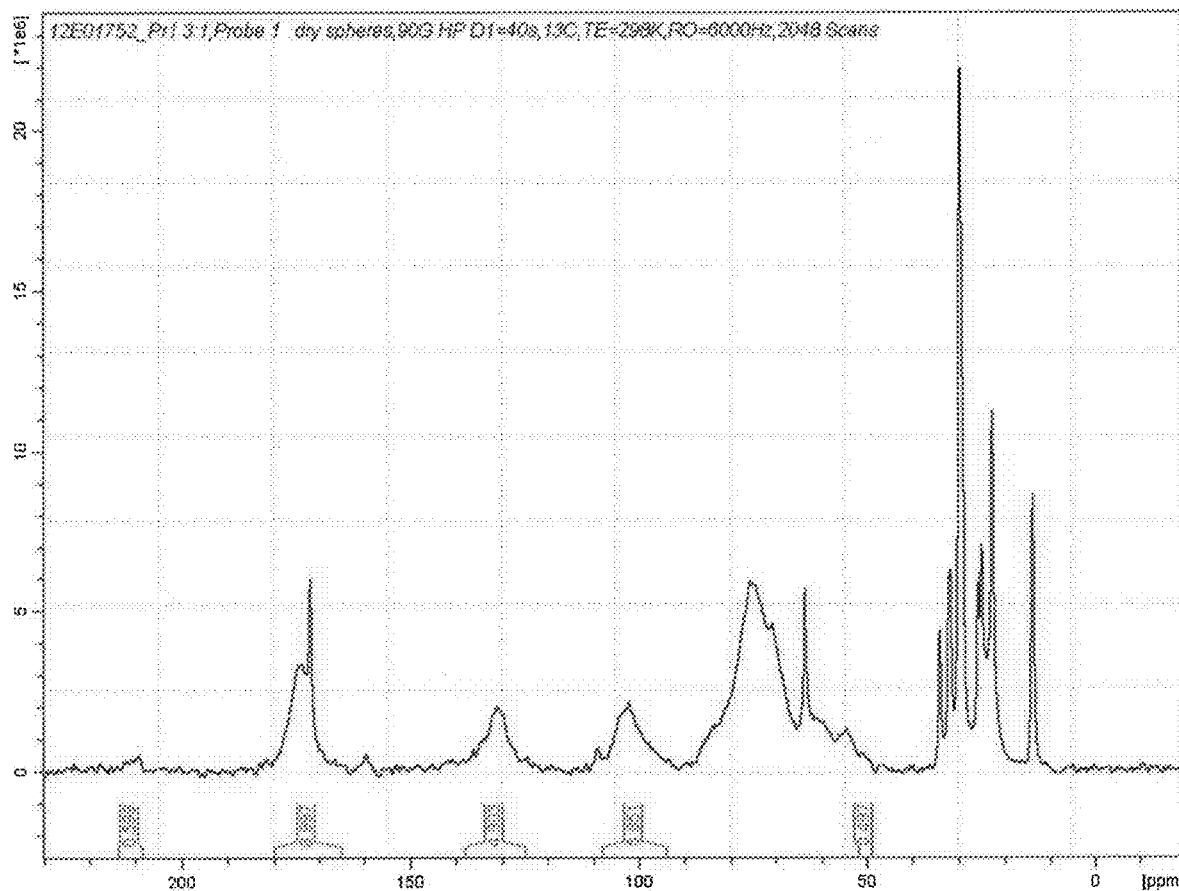
FIG. 5 represents the $^{13}C$ NMR spectrum obtained for the polymer of the spheres of Example 1.

Results:

FIG. 5 shows the curve obtained thereby

| Resonance (ppm) | Designation |
| --- | --- |
| 210/132/130/51 | TP (6 carbons) |
| 175 | Polymer and HA (C=O i.e. 4 carbons) |
| 103 | HA and KG (C$^1$ of polysaccharides i.e. 2 carbons for HA and 4 carbons for KG) |

ABBREVIATIONS

TP: terephthalate
HA: hyaluronate
KG: glucomannan

According to the calculations based on the integrals, the characterization of the polymer of the invention established that:
- the hyaluronate group represents 50% to 90%, more preferably 60% to 80% by weight of dry matter of the polymer of the invention;
- the glucomannan group (Gluc) represents 1% to 10%, more preferably 1% to 5% by weight of dry matter of the polymer of the invention;
- the group obtained from the cross-linking agent, i.e. the terephthalate group, represents 10% to 40%, more preferably 20% to 30% by weight of dry matter of the polymer of the invention.

Example 9

Examples of Compositions

Methods that are known to the skilled person were used to mix together the various parts A, B, C, D, E or F in order to prepare a composition in accordance with the present invention.

The "products of the invention" represent the spheres of the invention, preferably obtained in accordance with Example 1 and preferably suspended in an oily support (ethylhexyl palmitate) in an amount of 0.2%.

FORMULATION EXAMPLE

| | | |
|---|---|---|
| A | Water | qsp 100 |
| | Glycerin | 3 |
| | Magnesium Sulfate | 1 |
| B | Polyglyceryl-2 Dipolyhydroxystearate | 2 |
| | PEG-30 Dipolyhydroxystearate | 2 |
| | Propylheptyl Caprylate | 6 |
| | Dicaprylyl Carbonate | 6 |
| | Dibutyl Adipate | 6 |
| | Cetearyl Isononanoate | 7 |
| | Phenoxyethanol, Methylparaben, Propylparaben, Ethylparaben | 0.6 |
| C | Product of the invention | 0.01-10 |

The invention claimed is:

1. A sphere formed by a polymer of hyaluronate and glucomannan, said polymer consisting of one or more than one hyaluronate group and one or more than one glucomannan group, said one or more than one hyaluronate group and said one or more than one glucomannan group being cross-linked together via at least one ester bond wherein the one or more than one hyaluronate group of the polymer is of low weight average molecular weight in the range 10 kDa to 40 kDa and wherein the sphere has a D50 diameter measured by laser diffraction of 3 μm to 80 μm.

2. The sphere according to claim 1, wherein the sphere is dehydrated.

3. The sphere according to claim 1, wherein a cross-linking agent is used for interfacial cross-linking and the cross linking agent is an acid dichloride selected from the group consisting of terephthalic, sebacic, succinic, fumaric acid dichloride and a mixture thereof.

4. The sphere according to claim 1, wherein the glucomannan group of the polymer is obtained from a konjac glucomannan or esterified derivatives thereof.

5. The sphere according to claim 1, wherein the one or more than one glucomannan group of the polymer has a weight average molecular weight in the range 200 kDa to 2000 kDa.

6. A cosmetic or dermatological composition for topical administration, comprising at least one sphere according to claim 1 and a cosmetic or dermatological vehicle.

7. The cosmetic or dermatological composition for topical administration according to claim 6, wherein the sphere is included in the cosmetic or dermatological composition in a quantity in the range 0.0001% to 20% by weight of dry matter with respect to the total cosmetic or dermatological composition weight.

8. The cosmetic composition for topical administration according to claim 6, comprising at least one further ingredient of cosmetic interest selected from the group consisting of a filling agent, a tightening agent and a hydrating agent.

9. A sphere obtained by a process comprising the following steps:
   a) producing an emulsion:
      i) between at least a first phase consisting of one or more than one hyaluronate compound and one or more than one glucomannan compound, said compounds being soluble in said first phase; and
      ii) at least one second phase that is not miscible with the first phase;
   b) cross-linking said one or more than one hyaluronate compound and one or more than one glucomannan compound together in the presence of at least one cross-linking agent, said cross-linking agent being soluble in said second phase; and
   c) recovering spheres wherein the hyaluronate has a low weight average molecular weight in the range 10 kDa to 40 kDa and wherein the sphere has a D50 diameter measured by laser diffraction of 3 μm to 80 μm.

10. A method of cosmetic care for smoothing the contours of the skin and/or for plumping the epidermis and/or for filling out the epidermis, and/or for filling the surface of the epidermis and/or the mucous membranes, and/or for improving the hydration of the skin and/or for improving the elasticity of the skin and/or for preventing and/or treating the appearance of wrinkles in the epidermis comprising administering an effective amount of the sphere according to claim 1 to a human in need thereof.

11. The method according to claim 10 wherein the administering is topical application.

12. The sphere according to claim 1 wherein the one or more than one hyaluronate group of the polymer is obtained from hyaluronic acid or a salt of hyaluronic acid.

13. The method of cosmetic care according to claim 10 comprising the administering an effective amount of the sphere according to claim 1 as a moisture absorbing agent.

14. The cosmetic or dermatological composition for topical administration according to claim 7, wherein the polymer and/or the sphere is included in the cosmetic or dermatological composition in a quantity in the range 0.0005% to 10% by weight of dry matter with respect to the total cosmetic or dermatological composition weight.

15. The sphere according to claim 1 wherein the one or more than one hyaluronate group and said one or more than one glucomannan group are cross-linked together via a group originating from a cross-linking agent.

16. The sphere according to claim 1 wherein the one or more than one glucomannan group represents 1% to 5% by weight of dry matter of the polymer.

17. The sphere according to claim 9 wherein the one or more than one hyaluronate compound of the polymer is of low weight average molecular weight in the range 10 kDa to 40 kDa and the one or more than one hyaluronate compound is cross-linked with the one or more than one glucomannan compound via at least one ester bond.

18. The sphere according to claim 17 wherein the one or more than one hyaluronate compound and said one or more than one glucomannan compound are cross-linked together via a group originating from the cross-linking agent.

19. The sphere according to claim 1, wherein the one or more than one hyaluronate group represents 50% to 90% by weight of dry matter of the polymer.

20. The sphere according to claim 1, wherein the one or more than one glucomannan group represents 1% to 10% of dry matter of the polymer.

21. The sphere according to claim 15, wherein the one or more than one hyaluronate group is sodium hyaluronate and the glucomannan group is konjac glucomannan.

* * * * *